United States Patent [19]
Mueller et al.

[11] Patent Number: 5,840,075
[45] Date of Patent: Nov. 24, 1998

[54] DUAL LASER DEVICE FOR TRANSMYOCARDIAL REVASCULARIZATION PROCEDURES

[75] Inventors: Richard L. Mueller, Byron; Stuart D. Harman, San Jose, both of Calif.

[73] Assignee: Eclipse Surgical Technologies, Inc., Sunnyvale, Calif.

[21] Appl. No.: 702,024

[22] Filed: Aug. 23, 1996

[51] Int. Cl.⁶ ................................................... A61B 17/36
[52] U.S. Cl. .................................... 606/7; 606/11; 606/15
[58] Field of Search .......................... 606/3, 7–12, 15–16

[56] References Cited

U.S. PATENT DOCUMENTS

| | | |
|---|---|---|
| 4,532,400 | 7/1985 | Toida et al. . |
| 4,573,465 | 3/1986 | Sugiyama et al. ................... 128/303.1 |
| 4,583,539 | 4/1986 | Koulin et al. . |
| 4,658,817 | 4/1987 | Hardy ................................... 128/303.1 |
| 4,854,315 | 8/1989 | Stack et al. . |
| 4,917,083 | 4/1990 | Harrington et al. . |
| 5,074,862 | 12/1991 | Rausis . |
| 5,107,516 | 4/1992 | Dressel et al. . |
| 5,219,347 | 6/1993 | Negus et al. . |
| 5,304,167 | 4/1994 | Freiberg ...................................... 606/3 |
| 5,380,316 | 1/1995 | Aita et al. .................................... 606/7 |
| 5,620,439 | 4/1997 | Abela et al. .............................. 606/11 |

OTHER PUBLICATIONS

Mirhoseini et al., "Lasers in Cardiothoracic Surgery", in Lasers in General Surgery (Joffe, Editor), Williams and Wilkins, 216–232 (1989).

*Primary Examiner*—Francis Jaworski
*Attorney, Agent, or Firm*—Janet Kasier Castaneda; Christopher N. Sears

[57] ABSTRACT

A method of and apparatus for performing a transmyocardial revascularization procedure is disclosed which utilizes two laser power sources. A first laser source provides a coagulating or blanching effect on tissue and a second laser source capable of tissue ablation are supplied to a combined optical fiber bundle comprising a plurality of fibers which can be moved axially or rotatively by the operating physician. As the distal end of the fiber bundle is moved forward, bursts of laser energy therefrom may be programmed to first penetrate the epicardium with minimal bleeding and thereafter provide channels or pockets in the myocardium for causing or stimulating angiogenesis.

19 Claims, 5 Drawing Sheets

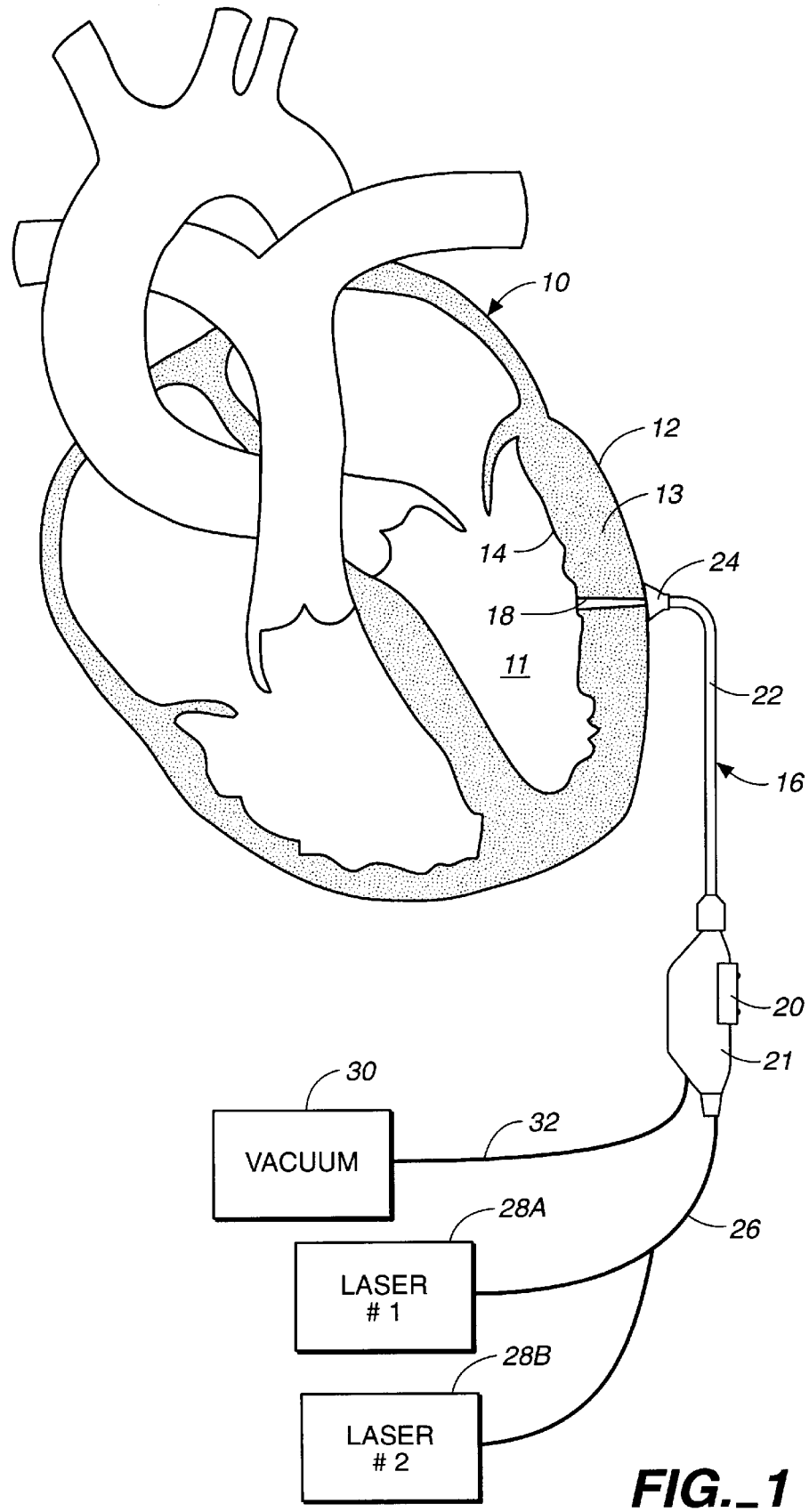
FIG._1

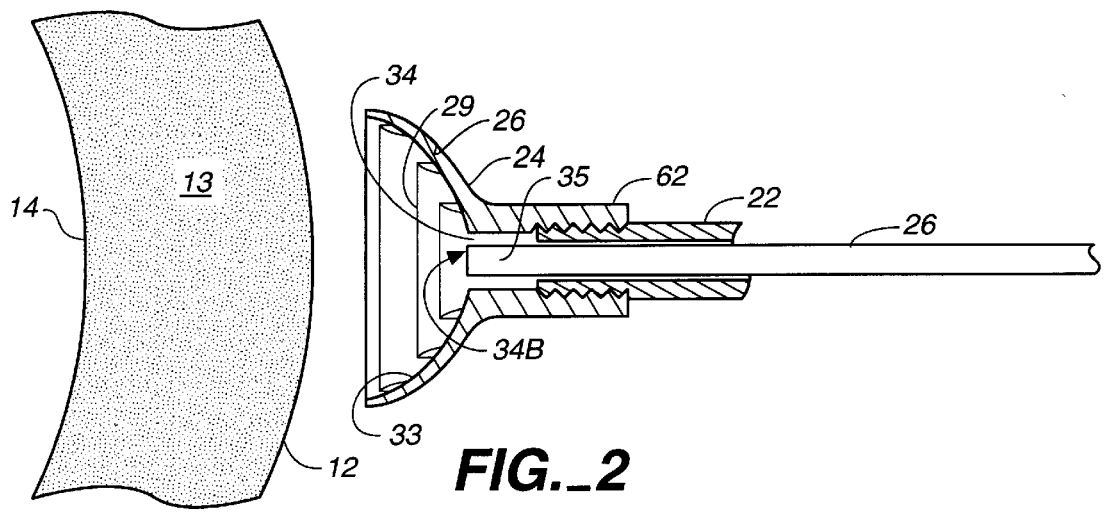
FIG._2
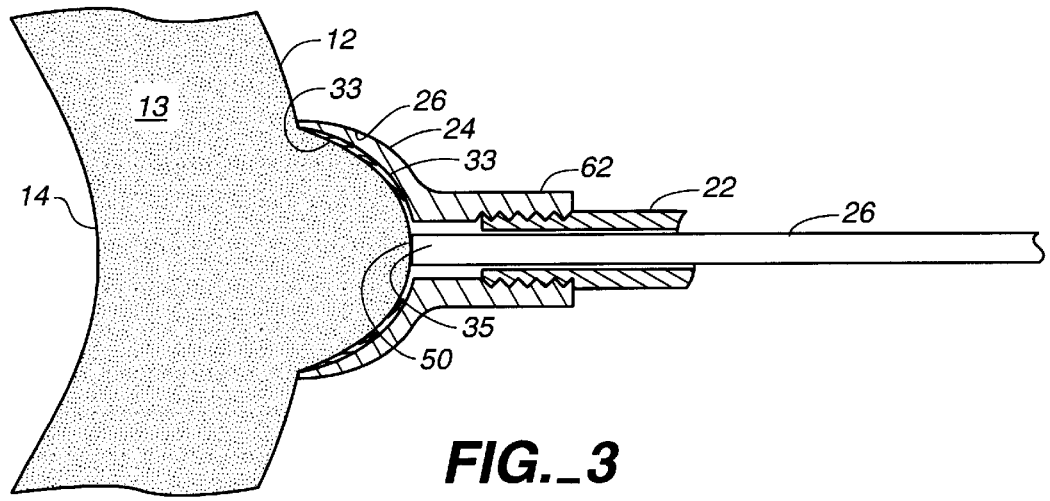
FIG._3
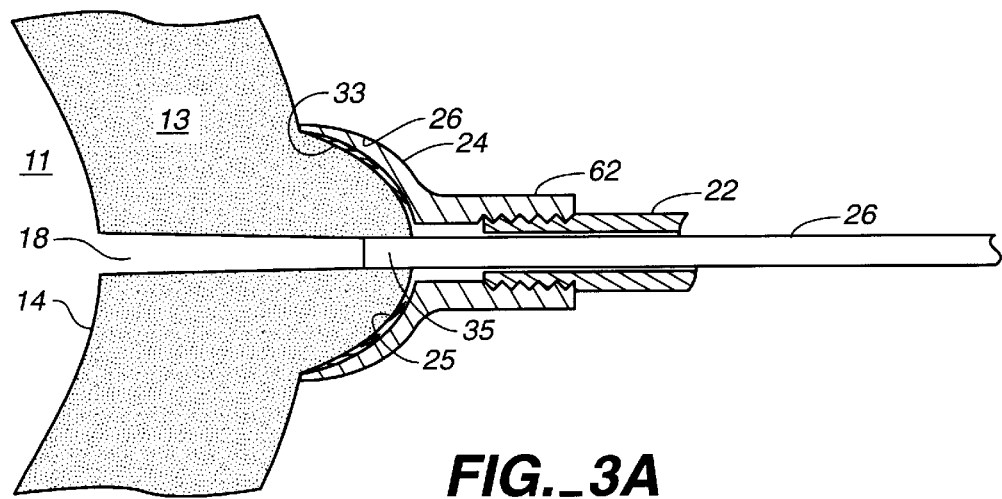
FIG._3A

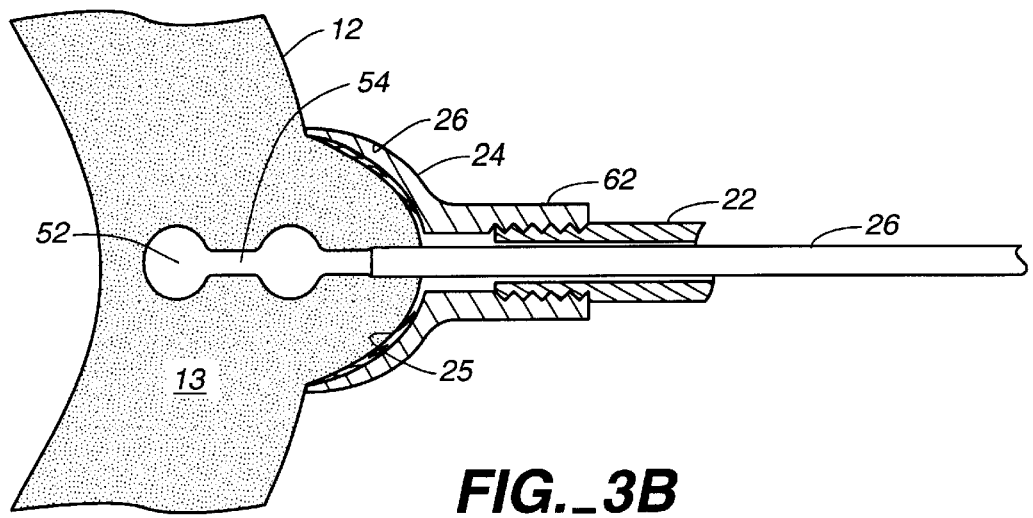
FIG._3B
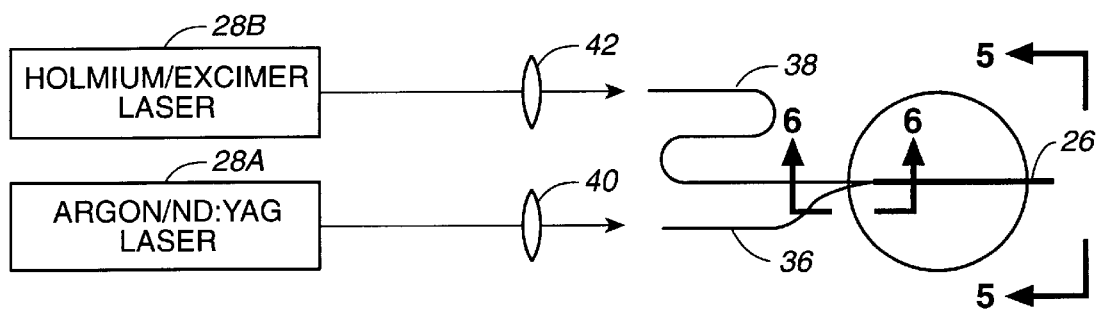
FIG._4
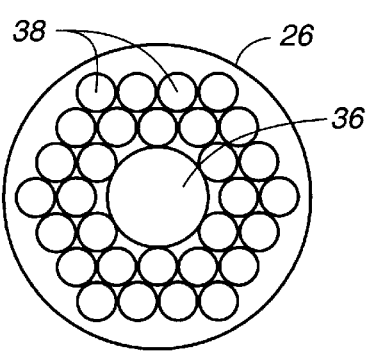 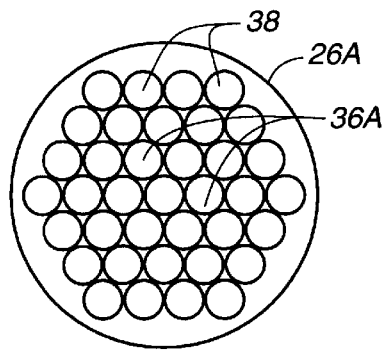
FIG._5          FIG._5A

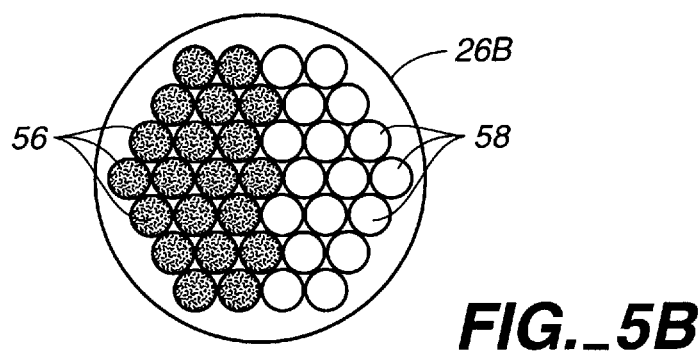
FIG._5B
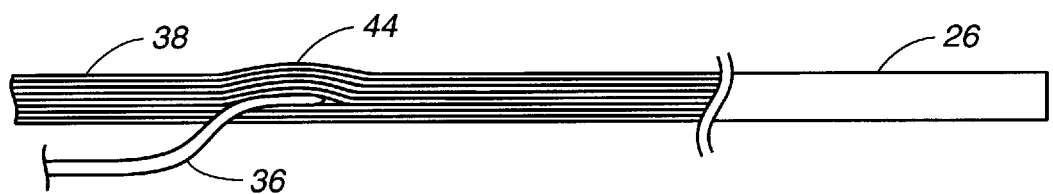
FIG._6
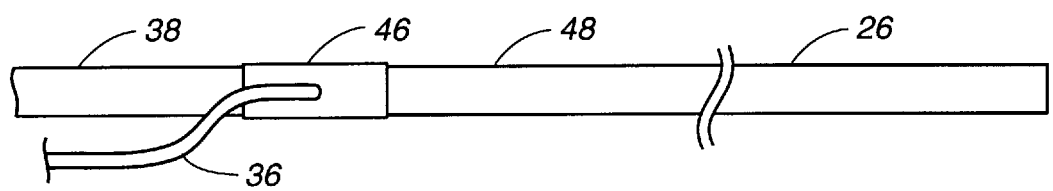
FIG._6A

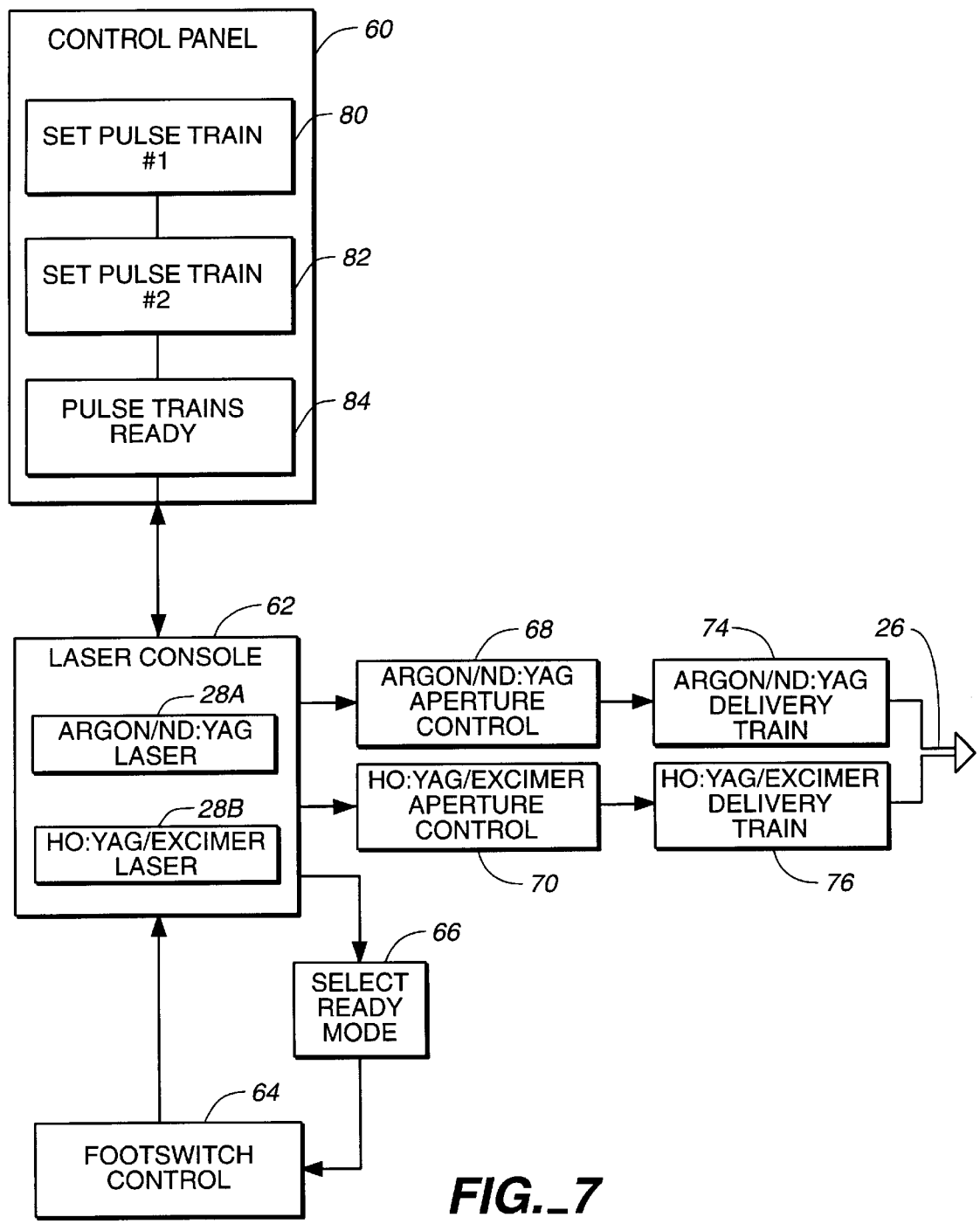
FIG._7

DUAL LASER DEVICE FOR TRANSMYOCARDIAL REVASCULARIZATION PROCEDURES

FIELD OF INVENTION

This invention relates to the field of laser surgery, and more particularly to an improved laser surgery device for use in procedures for increasing the flow of blood to heart muscle.

BACKGROUND OF THE INVENTION

To counteract the effects of cardiovascular disease medical science has developed a procedure known generally as Transmyocardial Revascularization (TMR). In such procedures, channels are formed in the ventricle wall of the heart with a laser. These channels provide blood flow to ischemic heart muscle. A history and description of this method has been documented by Dr. M. Mirhoseini and M. Cayton on "Lasers in Cardiothoracic Surgery" in Lasers in General Surgery (Williams & Wilkins; 1989) pp. 216–233.

As described therein, a CO2 laser was used to produce channels in the ventricle from the epicardium through the myocardium. This procedure followed a surgical incision in the chest wall to expose the heart. Laser energy was transmitted from the laser to the epicardium by means of an articulated arm device of the type commonly used for CO2 laser surgery. The beam was coherent and traveled as a collimated beam of laser energy through the epicardium, the myocardium and the endocardium into the left ventricle cavity. The epicardium received the highest energy density and therefore normally had the largest area of heart tissue removed compared with the endocardium which was approximately 1 cm from the epicardium. The resultant channel through the myocardium was funnel-like. One problem associated with the above procedure arose because laser perforation of the epicardium caused bleeding from it outwardly from the left ventricle after the procedure. External pressure by the surgeon's hand on the epicardium of the heart was often needed to stop bleeding from the ventricle to the outside through the hole produced by the laser in the epicardium. However, this procedure was usually only partially successful because it resulted in a significant amount of blood loss and/or an excessive amount of time required to stop the bleeding. Both factors could jeopardize the success of the revascularization procedure.

In a proposed improvement in a TMR procedure described in Hardy U.S. Pat. No. 4,658,817, a needle was added to the distal tip of an articulated arm system, with a beam of laser energy being passed through the lumen of the needle. The metal tip of the needle of the device was used to pierce most of the myocardium and the laser beam then was used to create the desired channel through the remaining portion of the myocardium and through the adjacent endocardium. In the Hardy procedure, the hollow needle used to deliver laser light was subject to being clogged by tissue or blood which could flow into the needle, thus blocking the laser light from impinging the myocardium. Also, the metal rim of the needle could be damaged by the intense laser light and leave contaminating metal remains within the myocardium which are potentially hazardous.

Another proposed TMR procedure is described in the Aita, et al U.S. Pat. No. 5,380,316. This patent describes an elongated flexible lasing apparatus which is guided to an area exterior to the patient's heart and irradiates the exterior surface to form a channel through the epicardium, myocardium and endocardium. Thus, in the Aita et al procedure, the epicardium was irradiated at a high energy density and therefore caused a relatively large area of heart tissue to be removed. Consequently, the Aita, et al procedure had the same problems and disadvantages as the prior Mirhoseini TMR procedure with respect to the aforementioned bleeding problem in the outer surface of the epicardium.

Still another problem with prior TMR procedures was that under certain operating conditions, channels created by laser action in the myocardium tended to close prematurely before sufficient angiogenesis could develop in the channels. One reason for this problem was that the characteristics of the laser used failed to achieve the optimum reaction with the heart muscle tissue. It is known that certain laser types provide different tissue reactions, and the present invention takes advantage of this basic phenomena.

It is therefore a general object of the present invention to provide an improved method and apparatus for performing laser myocardial revascularization that solves the problems of the aforementioned prior devices and procedures, increases the effectiveness of the TMR treatment and eliminates the problem of excessive bleeding from the patient's epicardium following the channel forming procedure.

A more specific object of the invention is to provide an improved method for penetrating the epicardium during a TMR procedure wherein a first laser beam is used to coagulate or preblanch the epicardial tissue prior to application of a second laser beam of higher energy level to pierce the epicardium without causing external bleeding therefrom.

Another object of the invention is to provide a TMR apparatus having optical fiber means connected to two separately controllable laser energy sources so that one laser can be used to coagulate or preblanch the epicardium and thereafter a second laser can be used to pierce the epicardium without causing bleeding therefrom.

Yet another object of the invention is to provide a device for use in a TMR procedure which uses a concave distal end member that contacts the outer surface of the epicardium, and then applies air suction during the procedure to draw the epicardium into the distal end member before triggering dual laser emissions at the epicardium to enable penetration thereof with minimal bleeding.

A further object of the invention is to provide a TMR laser apparatus wherein laser energy from two different laser sources can be preprogrammed to provide coordinated trains of laser pulses for first penetrating the epicardium and thereafter ablating the myocardium to form channels or pockets that create angiogenesis of the heart muscle.

SUMMARY OF THE INVENTION

The present invention comprises a method and apparatus for combined mechanical/laser myocardial revascularization of a human heart that fulfills the aforesaid objectives. The apparatus comprises a hand-held device with an elongated flexible lasing means or optical fiber bundle that can be inserted into the chest cavity of a patient. In one form, the device includes a detachable distal head end assembly including a circular disk having a central bore through which the distal tip of the fiber bundle can pass. The distal head assembly is preferably connected to a vacuum source so that the epicardium can be drawn into engagement with a concave inner surface of the distal head. The optical fiber bundle has separate fiber elements connected to two laser sources, including a central fiber or group of optical fibers surrounded by a plurality of outer optical fibers. In one phase of operation the central fiber is connected to a first laser energy source and the outer optical fibers are connected to a second laser source having a higher power level than the first laser source. The first laser source may be an Argon or Nd:YAG laser which has a coagulative or preblanching effect on tissue, and the second laser source may be a Holmium (Ho:YAG) or Excimer laser which has a more ablative effect on tissue. Alternatively, the laser sources may be switched, with the Holmium or Excimer laser being used for the central fiber means and the Argon or Nd:YAG laser being used for the outer fibers. In this mode, the outer fibers provide laser energy that coagulates tissue in the walls of the channel formed by the central Holmium or Excimer laser to help keep the channel open.

In the method according to the invention, the hand-held device is positioned so that its distal end member is against the outer epicardium surface. When a vacuum is applied, the epicardium is drawn into the concave distal end member so that the distal end of the optical fiber means is adjacent the epicardium surface. At this point, the laser source connected to the central fiber means is energized at its relative low power level to cause a coagulation or blanching of the epicardial tissue. Immediately thereafter, the outer fibers are energized from the second laser source at a higher power level to create a small opening in the epicardium. Following this, the optical fiber means is mechanically advanced into the myocardium as the laser is pulsed to create a channel extending through the endocardium into the ventricle cavity or to create stimulus zones that cause angiogenesis. The use of laser sources of high and low power levels provides for the preblanching or coagulation of the epicardium which diminishes or eliminates bleeding.

Other objects, advantages and features of the present invention will be apparent to those skilled in the art from the following detailed description and the accompanying drawings.

DETAILED DESCRIPTION OF DRAWING

FIG. 1 is a schematic view in section of a human heart showing revascularization of the myocardium utilizing an apparatus according to the present invention.

FIG. 2 is an enlarged view in elevation and in section showing a distal end portion of the device shown in FIG. 1.

FIG. 3 is an enlarged view in elevation and in section showing the device of FIG. 2 as it appears in use for forming an opening in the epicardium.

FIG. 3A is a view similar to FIG. 3, showing the formation of a channel in the myocardium.

FIG. 3B is a view similar to FIG. 3 showing the formation of revascularization pockets in the myocardium.

FIG. 4 is a diagrammatic view of the optical fiber bundle for the apparatus shown in FIG. 1 according to the invention.

FIG. 5 is a cross-section of the fiber bundle for the apparatus taken at line 5—5 of FIG. 4.

FIG. 5A is a cross-section of a modified form of fiber bundle for the apparatus of FIG. 4.

FIG. 5B is a cross-section of another form of fiber bundle for the apparatus of FIG. 4.

FIG. 6 is a fragmentary view showing the junction of two optical fiber elements forming the optical fiber bundle for the apparatus of FIG. 1.

FIG. 6A is a fragmentary view similar to FIG. 6 showing the fiber bundle junction covered by a sheath.

FIG. 7 is a block diagram of the dual laser revascularization system according to the invention.

FIG. 8 is a partial block diagram showing a modified form of the revascularization system.

DETAILED DESCRIPTION OF EMBODIMENT

With reference to the drawing, FIG. 1 diagrammatically depicts a human heart 10 with the outer wall of the left ventricle 11 exposed where a Trans-Myocardial Revascularization (TMR) procedure according to the invention is to be performed. Preliminary to the procedure the surgeon makes an incision in the patient's chest to expose the outer wall of the heart's left ventricle. In a human heart the wall of the left ventricle is comprised of an outer layer, the epicardium 12, the main muscle thickness or myocardium 13, and the inner layer or endocardium 14. The epicardium is comprised of a smooth, moist serous membrane which is somewhat tougher than the other tissue layers of the heart muscle.

In performing a TMR procedure utilizing the present invention, the surgeon preferably utilizes a hand-held device 16 such as shown in FIG. 1 which is manipulated and operated to form a series of revascularization channels 18 in the myocardium of the patient's heart at selected spaced apart locations. The device 16 is described in greater detail in U.S. application Ser. No. 08/628,456, filed on Apr. 5, 1996 which is assigned to the assignee of the present application. Essentially, it includes a hand held body 21 with an elongated neck portion 22 having an enlarged distal head member 24. An optical fiber bundle 26 extends from its distal end within the head member 24 through the neck portion 22 and the body 21. At its proximal end, the fiber bundle is connected to two separate laser sources 28A and 28B. The device 16 enables the operating physician to position the enlarged distal head member 24 against the outer surface of the epicardium and then move the laser transmitting fiber bundle 26 through the head member and into position adjacent the epicardial surface 12. A control 20 on the device enables the fiber bundle, which is attached to the control within the body 21, to be advanced or retracted axially when required. A vacuum pump 30 is preferably provided which is connected by a flexible conduit 32 through the device 16 to the distal head member 24 so that a suction force at the distal head member will draw the epicardium against its inner end surface 33.

As shown in FIG. 2, the end surface 33 of the distal end member 24 preferably has a concave shape with a central opening 34 through which the fiber bundle 26 extends so it can move freely with ample clearance. Preliminary to a typical procedure the distal tip 35 of the fiber bundle 26 is positioned right at the central opening 34 so that when the concave end face of distal end member engages the epicardium, as shown in FIG. 3, the distal tip of the fiber bundle is closely adjacent the epicardial surface.

In accordance with the principles of the invention and as shown schematically in FIG. 4, the fiber bundle 26 is comprised of two fiber elements which are connected to separate laser sources having different performance characteristics. A central optical fiber member 36 of the bundle is connected to one laser source 28A and a surrounding group of outer fibers 38 are connected to the second laser source 28B. As shown in FIG. 5, the central member 36 may be a unitary optical fiber strand, having a diameter of around 0.2–0.6 mm, and it is surrounded by a plurality of smaller fibers forming the second fiber element. However, as shown in FIG. 5A, the central member 36 may also be comprised of a plurality (e.g. 7) of smaller fiber strands 36A, each having a diameter of around 0.1 mm. For both embodiments, the outer fibers 38 also have a diameter of 0.1 mm. When bundled together, the fibers are held in place by a suitable potting compound and the entire fiber bundle 26 is enclosed in a protective sheath in the conventional manner.

It has been found that lasers of different types provide different results when applied to various forms of human tissue during medical procedures. For example, a Ho:YAG Holmium or Excimer laser beam provides an energy level that effectively vaporizes and/or ablates muscle tissue, and thus it is particularly adaptable for forming channels of pockets within the myocardial tissue of the heart. An Nd:YAG or Argon laser, however provides a lower energy level that tends to coagulate or blanch tissue without totally ablating it. Thus, in accordance with the present invention the aforesaid two types of laser energy are employed to enable a more efficient and effective TMR procedure.

In one embodiment of the invention, shown in FIG. 4, the Argon/Nd:YAG laser source 28A is transmitted through a focusing lens 40 and into the central fiber element 36. The Holmium (Ho:YAG) or Excimer laser source 28B is furnished through a focusing lens 42 to a single fiber optic which is optically coupled to a distal group of optical fibers 38. At a distance from the laser sources, the optical fibers 36 and 38 are combined at a junction 44 as shown in FIG. 6, to form the composite fiber bundle 26. The junction 44 is covered by suitable joint 46 which surrounds a protective sheath 48 around the fiber bundle 26, (See FIG. 6A).

In carrying out the method of the invention, as shown in FIG. 3, after the epicardial tissue is drawn by vacuum force against the concave surface 33 of the distal end member 24, the Argon laser 28A is energized to emit a beam of relatively low power laser energy from the central fiber 36 of the distal tip 35 of the fiber bundle to preblanch or coagulate the tissue of the epicardium 12. Immediately thereafter, the second Holmium or Excimer laser 28B is energized through the outer optical fibers 38 at a relatively higher energy level to form a small opening 50 in the preblanched area of the epicardium. Following activation of the second laser 28B, the fiber bundle 26 can be advanced axially by the device 16 through the opening 50 in the epicardium and into the myocardium. Because of the two step laser procedure in penetrating the epicardium, particularly the coagulating effect of the Argon or Nd:YAG laser in the central fiber 36, little or no bleeding occurs from the opening 50.

Once the distal tip 35 of the fiber bundle 26 has moved into the myocardium 13, one or both of the laser sources are activated to complete the TMR procedure. As shown in FIG. 3A, the second Holmium or Excimer laser 28B may be activated through the outer fibers 38 with sufficient energy to create a channel 18 that extends through the myocardium and the endocardium into the ventricle chamber 11, or the fiber may continue to be manually advanced into the ventricle and the laser 28B activated upon withdrawal to create the channel 18.

Alternatively, as shown in FIG. 3B, the physician may elect to carry out a stimulus procedure by creating ablated pockets 52 within the myocardium 13 which are connected by temporary channels 54. The pockets 52 are created by bursts of laser energy emitted from the outer optical fibers 38 connected to the Holmium or Excimer laser source when the fiber bundle 26 is advanced through the myocardium. Laser energy from the central fiber or fibers 36 is emitted as the fiber bundle is advanced to form a relatively narrow temporary channel 54. The fiber bundle 26 may or may not be stopped as laser energy at the higher level from the outer fibers 38 is emitted to form the ablated pocket 52. Details of similar stimulus procedures are disclosed in U.S. application Ser. No. 08/664,956, filed Jun. 13, 1996, which is assigned to the assignee of the present application.

Under some circumstances it may be advantageous to use a modified form of the invention wherein the central optical fiber 36 is connected to the Holmium or Excimer laser source 28B and the outer fibers 38 of the composite fiber element 26 are connected to the Argon laser source 38A. In this embodiment, both lasers are pulsed simultaneously to form a small opening in the epicardium. The Argon laser energy from the outer fibers 38 causes a coagulation effect on the peripheral tissue of the epicardium opening to quench a bleeding tendency. With the epicardium opening thus formed, the composite fiber element is pushed through the epicardium opening and into the myocardium. As this occurs, either or both laser sources are pulsed to form a channel 18 in the myocardium and through the endocardium into the left ventricle chamber. As the channel is formed, the physician would add Argon laser energy in the outer fibers to increase the effect of coagulating tissue on the walls of the channel. This causes an increased thermal effect triggering more extensive injury and healing or angiogenesis response.

In another modified form of the invention, shown in FIG. 5B, a fiber bundle 26B is comprised entirely of a plurality of small strands. Here, the bundle is divided into hemispherical sectors 56 and 58. One sector 56 on one side of the fiber bundle is connected at its proximal end to the Holmium laser source 28B, and the other sector 58 is connected at its proximal end to the Argon laser source 28A. In this embodiment, when the multi-stranded fiber element 26B is used, it is rotated back and forth in a circular path as it is moved forward. Thus, as the fiber element moves axially, two types of laser energy from its distal tip sweep over the tissue in its path so that the tissue impinged receives both an ablation effect from the Holmium laser energy and also a coagulative effect from the Argon laser energy.

In the operation of a TMR laser system according to the invention, a timing device or computer is preferably used to program the two laser sources to provide an optimum stream of pulses that will produce a desired result with each procedure. Each stream of pulses which are delivered to the heart to form one channel (or a series of ablated pockets) may be considered as analogous to a train which consists of discrete cars or individual pulses. Variability may exist in different trains with respect to how many cars (pulses) are in the train, the size (energy) and repetition rate (speed) of car or pulse. Using a computer, the physician is able to preset and provide a memory for the number of pulses to be delivered per channel and also preselect the energy and repetition rate for each of the discrete pulses in the pulse train.

FIG. 7 shows diagrammatically how a control panel 60 of a computer or CPU (not shown) is connected to a console 62 for two separate laser energy sources, namely an Argon or Nd:YAG laser 28A and a Holmium (Ho:YAG) or Excimer laser 28B. The console is controlled by a foot switch control 64. An enable switch 66 allows the user to select a ready mode, which arms the laser so when the footswitch pedal is depressed, the CPU causes the laser to fire and opens appropriate shutters to deliver energy into the fiber optic delivery systems. The Argon or Nd:YAG and Holmium or Excimer lasers are connected to separate aperture control means 68 and 70. The Argon or Nd:YAG control means is connected to the proximal end of the optical fiber element whose distal end emits Argon or Nd:YAG laser energy, and similarly the Holmium or Excimer control means is connected to the other optical fiber element that emits energy from its distal end. The computer (CPU)/memory unit (not shown) connected to the control panel enables pulses from the Argon or Nd:YAG and Holmium or Excimer lasers during each procedure to be preprogrammed to be superimposed, alternate, or overlap in time. In the arrangement of FIG. 7, separate delivery trains of pulses 74 and 76 are transmitted to the fiber bundle 26.

The control panel 60 for presetting the laser pulse parameters during each procedure may comprise a pair of input control buttons 80 and 82. For each laser, the wavelength, exposure mode, duration time and power may be preset. For example, with reference to the system of FIG. 7, the first button 80 may be utilized to select the Argon or Nd:YAG laser having a continuous wave (CW) mode, a pulse duration time of 0.5 sec with power at 3 watts. The second button 82 is used to select the Holmium or Excimer laser having a pulsed mode, e.g., selecting two pulses at a repetition rate of 10 pulses per sec and a power of 8 watts. Once all of the parameters for the two lasers have been programmed, a third or ready button 84 is pressed to put the laser console 62 in ready condition. Now, when the physician has the instrument such as device 16 in position, the foot switch 64 can be activated and the preprogrammed train of pulses will perform their channel forming function through the epicardium and myocardium of the patient's heart.

From the foregoing it should be apparent that the present invention provides a highly versatile and effective two laser TMR system that enables the physician to first penetrate the epicardium with minimal bleeding and then form ablated pockets or channels that remain patent for a longer period, thereby enhancing the revascularization process. The lasers used in the embodiments described are examples only. Other lasers and combinations thereof could be used within the scope of the invention including varying power levels of holmium and excimer lasers.

To those skilled in the art to which this invention relates, many changes in construction and widely differing embodiments and applications of the invention will make themselves known without departing from the spirit and scope of the invention. The disclosure and the description herein are purely illustrative and are not intended to be in any sense limiting.

What is claimed is:

1. A method for revascularizing a patient's heart comprising the steps of:
    providing access to a ventricle chamber sidewall of the patient's heart for an optical fiber means connected at its proximal end to laser source means and having a distal end for emitting laser energy at selected intervals;
    manipulating and placing the fiber means' distal end near a surface of the ventricle location;
    activating the laser source means during a first time period to provide an initial laser emission at a first power level at a target area on the surface of the ventricle;
    activating the laser source means during a second time period following the first time period to provide a second laser emission at a second power level that creates an opening in the ventricle at the target area without causing substantial bleeding at the opening;
    moving the optical fiber means axially forward through the opening; and
    reactivating the laser source means at the second power level to form a revascularizing channel or an ablated pocket within myocardium.

2. The method of claim 1 wherein in the step of providing a laser source means, the laser source means includes at least two different laser sources of different wavelengths.

3. The method of claim 2 wherein the laser source means are energized at different power levels as the fiber means is moved axially to create stimulation pockets connected by temporary channels in the myocardium.

4. The method of claim 2 wherein in the step of providing a laser source means, the laser source means includes a central fiber means connected to the first laser means and an outer fiber means surrounding the central fiber means connected to the second laser means.

5. The method of claim 4 wherein in the step of providing a laser source means, the central fiber means includes a plurality of bundled optical fibers.

6. The method of claim 4 wherein in the step of providing a laser source means, the first laser means is an argon laser and the second laser means is a Holmium (Ho:YAG) laser.

7. The method of claim 4 wherein in the step of providing a laser source means, the first laser means is a Nd:YAG laser and the second laser means is a Holmium (Ho:YAG) laser.

8. The method of claim 4 wherein in the step of providing a laser source means, the first laser means is an Argon laser and the second laser means is an Excimer laser.

9. The method of claim 4 wherein in the step of providing a laser source means, the first laser means is a Nd:YAG laser and the second laser means is an Excimer laser.

10. The method of claim 1 including the step of providing laser pulses at the first power level to cause coagulation of the tissue within the channel as it is formed by the laser source means at the second power level.

11. The method of claim 1 wherein the step of activating the laser source means during a second time period following the first, and the step of moving the optical fiber means axially forward through the opening and the step of reactivating the laser source means at the second power level occurs almost simultaneous while rotating the optical fiber means.

12. A surgical apparatus for revascularizing a patient's heart, the apparatus comprising:
    an optical fiber bundle having first and second fiber elements each connected at their proximal ends to a separate source of laser energy, the first fiber element being connected to a first laser source means for delivering laser energy for blanching or coagulating heart tissue having a first power, the first fiber element includes at least one centrally located optical fiber strand in the optical fiber bundle's distal end and the second fiber element connected to a second laser source means for delivering laser energy for ablating heart tissue having a second power different from the first power, the second fiber element includes peripherally located optical fiber strands in the optical fiber bundle's distal end;
    means for manipulating the fiber bundle and moving its distal end axially in preselected increments; and
    means for controlling pulses of laser energy from the first and second fiber elements.

13. The apparatus of claim 12 wherein the first fiber element is a single optical fiber strand and the second fiber element includes a plurality of single fiber strands.

14. The apparatus of claim 12 wherein the first and second fiber elements are comprised of a plurality of fiber strands.

15. The apparatus of claim 12 wherein the first and second laser source means is selected from the group consisting of an Argon, Nd:YAG, Holmium (Ho:YAG) and Excimer type lasers.

16. The apparatus of claim 12 wherein the means for controlling includes memory means for preprogramming a train of laser pulses from each of the fiber elements, and switch means for emitting the laser pulses at preselected intervals.

17. A surgical apparatus for revascularizing a patient's heart, the apparatus comprising:

an optical fiber bundle having first and second fiber elements each connected at their proximal ends to a separate source of laser energy, the first fiber element being connected to a first laser source means for delivering a first power capable of blanching or coagulating heart tissue, and the second fiber element connected to a second laser source means for delivering a second power different from the first power and capable of ablating heart tissue, the first and second fiber elements each include a plurality of optical fiber strands that cross-sectionally form a substantially semi-circular area at the optical fiber bundle's distal end;

means for rotating the fiber bundle and moving the fiber bundle's distal end axially in preselected increments; and means for controlling pulses of laser energy from the first and second fiber elements.

18. The apparatus of claim 17 wherein the first and second laser source means is selected from the group consisting of Argon, Nd:YAG, Holmium (Ho:YAG) and Excimer type lasers.

19. The apparatus of claim 17 wherein the means for controlling includes memory means for preprogramming a train of laser pulses from each of the fiber elements, and switch means for emitting the laser pulses at preselected intervals.

* * * * *

UNITED STATES PATENT AND TRADEMARK OFFICE
CERTIFICATE OF CORRECTION

PATENT NO. : 5,840,075
DATED : Nov. 24, 1998
INVENTOR(S) : Richard L. Mueller and Stuart D. Harman It is certified that error appears in the above-identified patent and that said Letters Patent is hereby corrected as shown below:

Title Page: in the Attorney, Agent, or Firm section, after "Janet", delete "Kasier", and add--Kaiser--.

Column 3, lines 66-67: delete-"Fig. 8 is a partial block diagram showing a modified form of the revascularization system."

Signed and Sealed this

Seventh Day of December, 1999

Q. TODD DICKINSON

Attest:

Attesting Officer

Acting Commissioner of Patents and Trademarks